(12) United States Patent
Siochi

(10) Patent No.: US 6,330,300 B1
(45) Date of Patent: Dec. 11, 2001

(54) HIGH DEFINITION INTENSITY MODULATING RADIATION THERAPY SYSTEM AND METHOD

(75) Inventor: Ramon Alfredo Carvalho Siochi, Apex, NC (US)

(73) Assignee: Siemens Medical Solutions USA, Inc., Iselin, NJ (US)

(*) Notice: Subject to any disclaimer, the term of this patent is extended or adjusted under 35 U.S.C. 154(b) by 0 days.

(21) Appl. No.: 09/649,286

(22) Filed: Aug. 23, 2000

(51) Int. Cl.⁷ ........................................ A61N 5/10
(52) U.S. Cl. ............................. 378/65; 378/147
(58) Field of Search ....................... 378/65, 147, 150, 378/108

(56) References Cited

U.S. PATENT DOCUMENTS

| | | | |
|---|---|---|---|
| 5,663,999 | 9/1997 | Siochi | 378/65 |
| 5,724,403 | 3/1998 | Siochi et al. | 378/150 |
| 6,052,430 * | 4/2000 | Siochi et al. | 378/65 |
| 6,128,366 * | 10/2000 | Siochi | 378/65 |
| 6,134,296 * | 10/2000 | Siochi | 378/65 |

* cited by examiner

Primary Examiner—Robert H. Kim
Assistant Examiner—Irakli Kiknadze

(57) ABSTRACT

A method for controlling radiation delivery from a radiation source to a treatment area with a multi-leaf collimator. The method includes dividing the treatment area into a plurality of cells each having a predefined treatment intensity level and defining an edge margin on a portion of the cells. The method further includes defining one or more treatment fields by longitudinally positioning leaves of the multi-leaf collimator to block radiation from some of the cells. The edge margin has an intensity level different than the predeined intensity level of the cell. The longitudinal positions of leaves of the multi-leaf collimator are adjusted so that the leaves cover the edge margins of the cells in at least one of the treatment fields to deliver less radiation to said edge margin than the rest of the cell. A system for controlling radiation delivery to the treatment area from the radiation source is also disclosed.

14 Claims, 9 Drawing Sheets

HIGH DEFINITION INTENSITY MODULATING RADIATION THERAPY SYSTEM AND METHOD

FIELD OF THE INVENTION

The present invention relates generally to a radiation emitting device, and more particularly, to a system and method for delivering radiation treatment.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

In such intensity modulation, borders between critical structures and tumor volumes are sometimes not well approximated with a standard one centimeter width leaf which provides a one centimeter by one centimeter grid (cell size) over the intensity map. A higher resolution than typically provided with the one centimeter leaf is often required. One possible solution is to provide a collimator with thinner leaves. However, the additional hardware required for the additional leaves is expensive, adds weight to the system, may reduce clearance between the treatment head and the patient, and may decrease reliability and life of the system.

Another possible solution is to define intensity maps with a very small cell size (e.g. 2 mm in the direction of movement of the leaf). One drawback to this is that the intensity map becomes very complex with many of the high resolution cells providing no benefit since they are not located adjacent critical structures. The high resolution is typically important only at a border of the treatment field, near regions containing critical structures.

Accordingly, there is therefore, a need for a system and method for defining an intensity map that is deliverable with a conventional multi-leaf collimator at a higher spatial resolution.

SUMMARY OF THE INVENTION

A method and system for controlling radiation delivery to a treatment area from a radiation source are disclosed. In one aspect of the invention, a method generally includes dividing the treatment area into a plurality of cells each having a predefined treatment intensity level and defining an edge margin on at least a portion of the cells. The edge margin has an intensity level different than the predefined intensity level of the cell. The method further includes defining one or more treatment fields by longitudinally positioning leaves of the multi-leaf collimator to block radiation from some of cells. The method further includes adjusting a longitudinal position of leaves of the multi-leaf collimator such that the leaves cover the edge margin in at least one of the treatment fields to reduce the amount of radiation delivered to said edge margin.

The edge margin may be a periphery edge margin for cells located on a border of the treatment area or an internal area within a border of the treatment area that is shielded during radiation delivery.

A system of the present invention generally includes a collimator having multiple leaves for blocking radiation from the radiation source and defining an opening between the radiation source and the treatment area. The system also includes a processor operable to receive cell and edge margin data, position the leaves to define at least one treatment field based on the cell sizes and intensity levels and adjust the leaf positions to reduce the amount of radiation delivered to said edge margins.

The collimator is preferably rotatable about a radiation beam emitted from the radiation source to deliver radiation to a first treatment field with the leaves extending longitudinally along the first axis and a second treatment field with the leaves extending longitudinally along a second axis. The first axis is generally orthogonal to the second axis.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
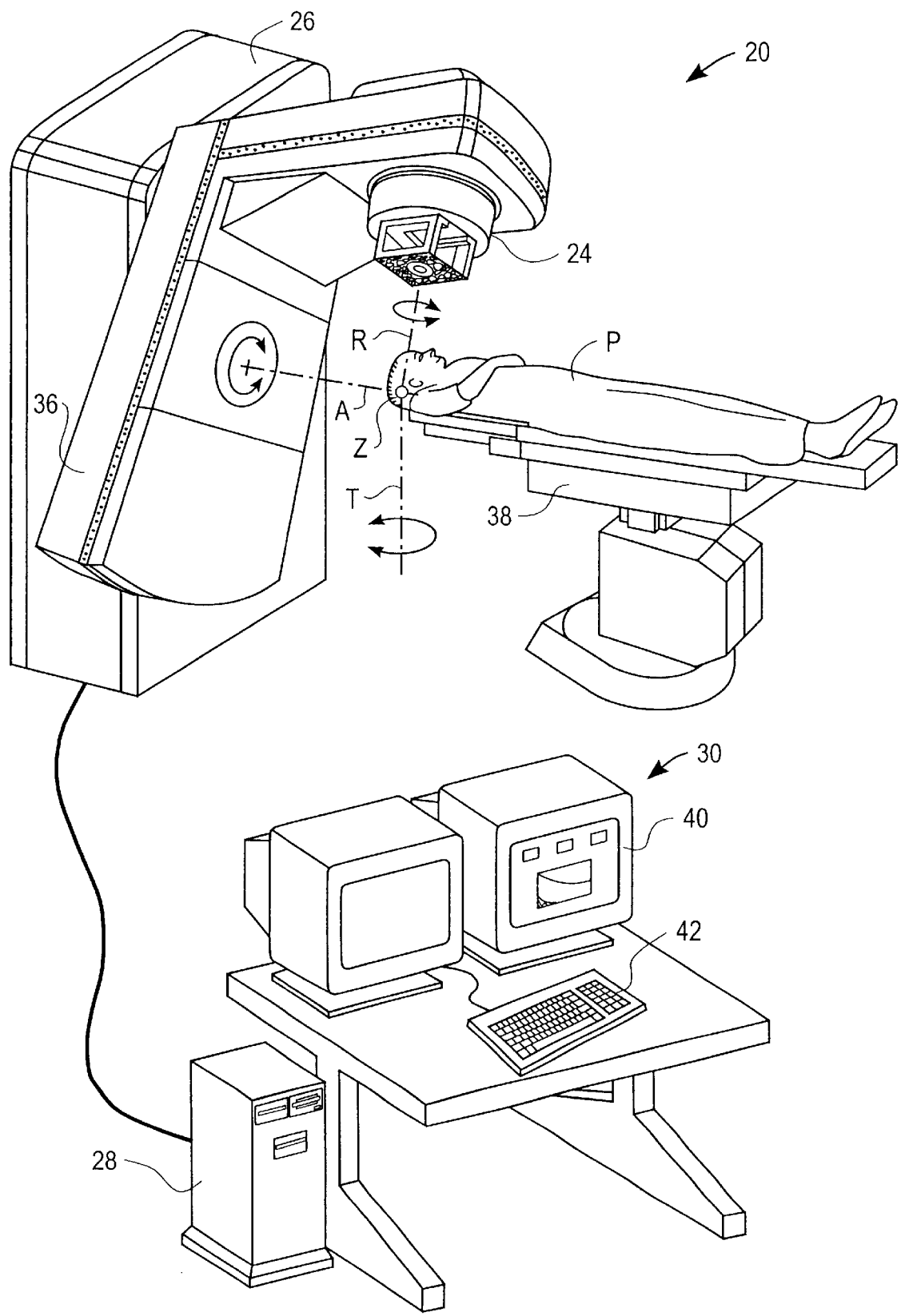
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated) The zone to be treated is located at an isocenter defined by the intersection of the rotational axis A of the gantry 36, rotational axis T of treatment table 38, and the radiation beam axis R. The rotatable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
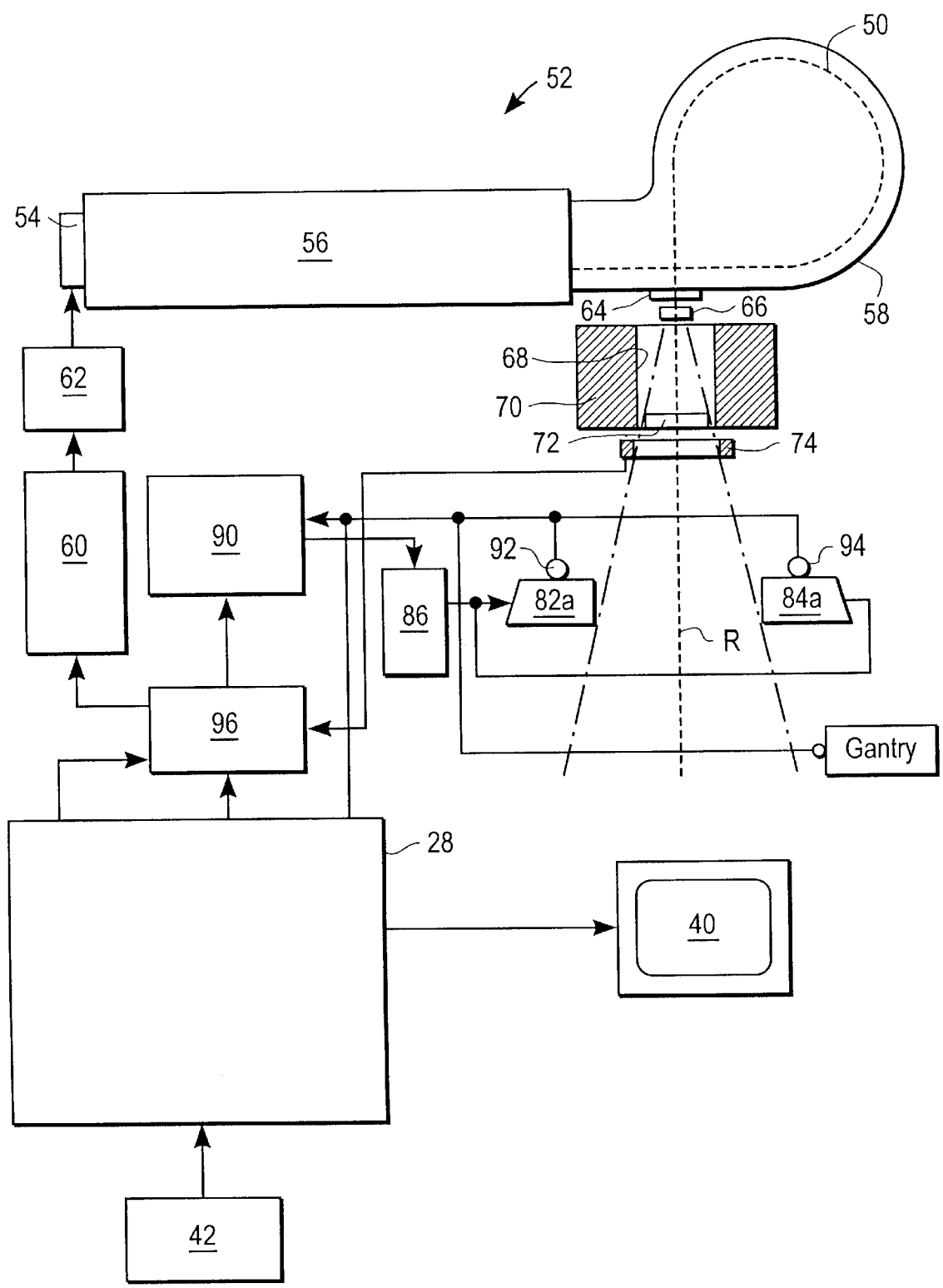
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
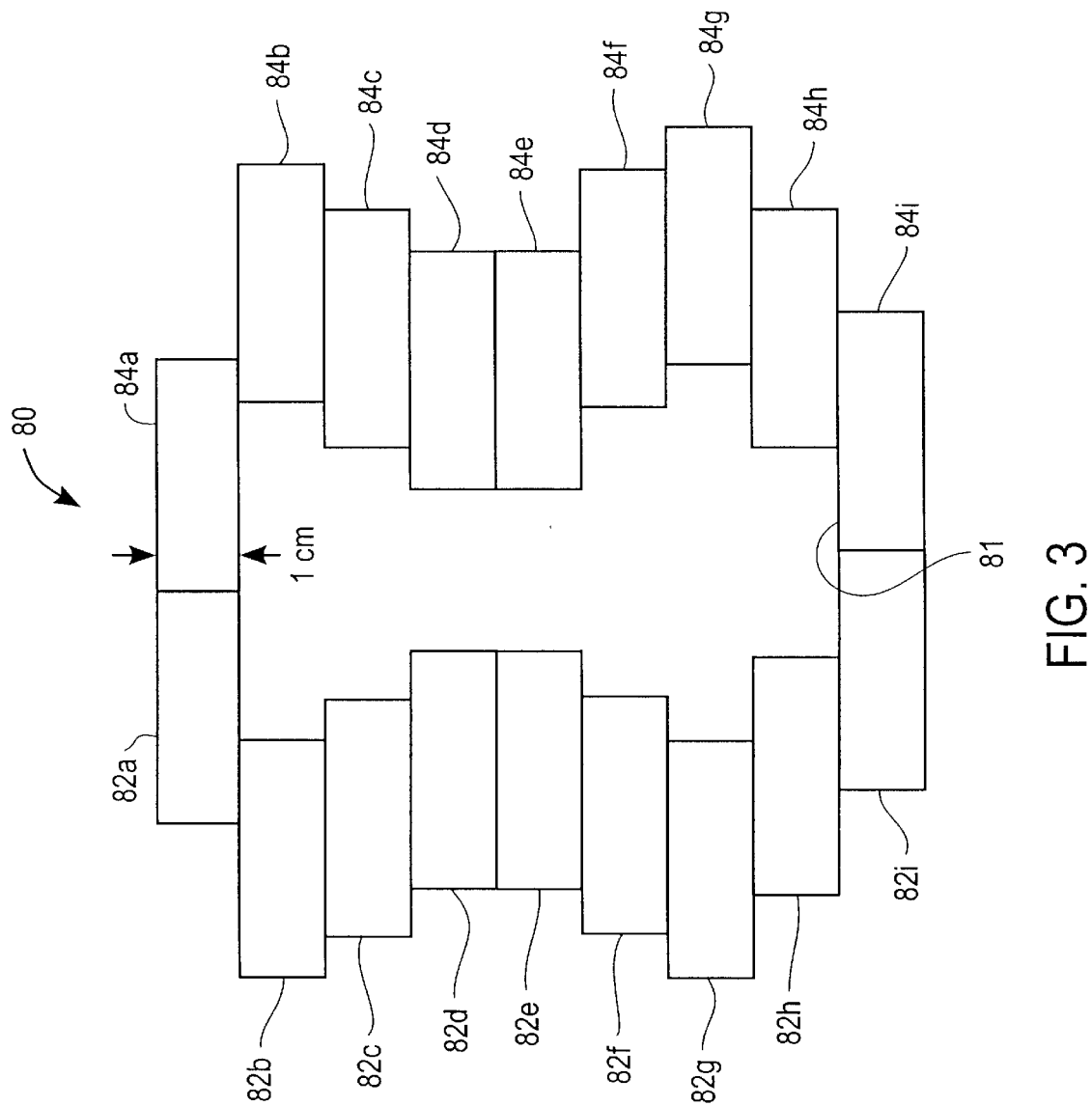
FIG. 3 is a schematic illustrating leaves of a multi-leaf collimator positioned for treatment in the radiation treatment device of FIG. 1.

A beam shielding device, generally indicated at 80, is provided in the path of the beam 50 to define a radiation field 81 (FIGS. 2 and 3). The beam shielding device 80 includes a plurality of opposing plates or leaves 82a–i and 84a–i, only two of which are shown in FIG. 2 for simplification. FIG. 3 illustrates leaves 82a–i and 84a–i (forming leaf pairs 82a and 84a, 82b and 84b, . . . , 82i and 84i) of a multi-leaf collimator mounted between the radiation source and patient and positioned to define a treatment field by delimiting the electron beam 50. The leaves 82a–i, 84a–i typically have a one centimeter width and are substantially impervious to the emitted radiation so that they block healthy tissue from the radiation.

The leaves 82a–i, 84a–i are movable in a direction generally perpendicular to axis R by a drive unit 86 (which is shown in FIG. 2 only with respect to plate 82a) to change the size of the irradiated field so that the distribution of radiation over the field does not need to be uniform (i.e., one region may be exposed to a higher dose than another region). The drive unit 86 includes an electric motor which is coupled to the plate 82a and controlled by a motor controller 90. Position sensors 92, 94 are also coupled to plates 82a, 84a, respectively, for sensing their positions. The drive unit 86 drives the plate 82a in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82a, 84a. The central processing unit 28 controls execution of the program and the opening and closing of the collimator plates 82a, 84a to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention. The treatment device 20 described above is provided as an example of a device for use in delivering a treatment developed by the optimization process described below.

Figure 4:
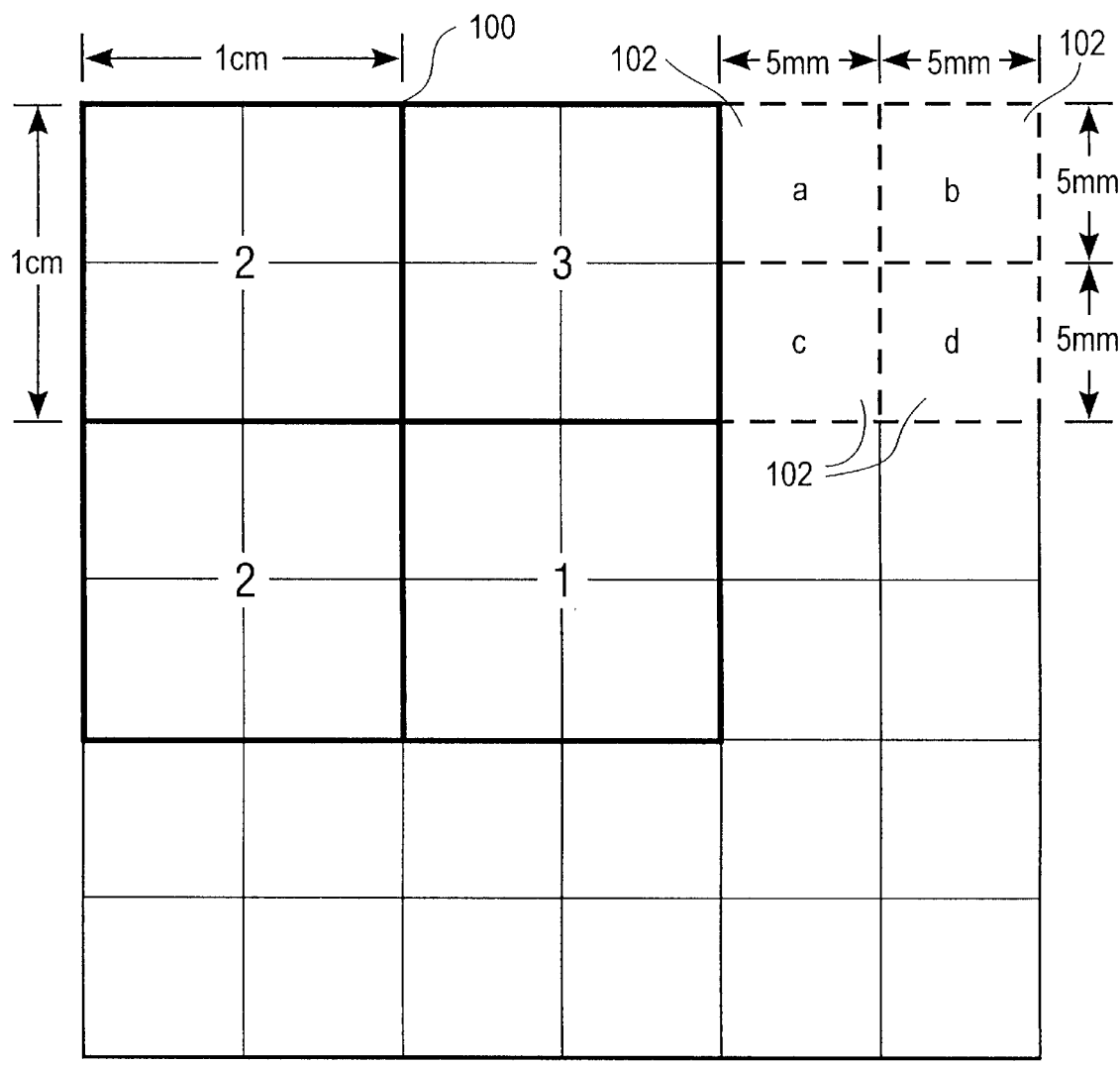
FIG. 4 is a schematic illustrating cells located in an intensity map.

FIG. 4 illustrates an intensity map having a plurality of 1 cm×1 cm macrocells 100 (indicated by dark lines), each cell defining a particular level of radiation to be administered. The intensity map specifies a number of fields defining optimized intensity levels at each cell. Some of the cells are positioned on a border of the treatment area, with a portion of the cells located external to the treatment area. There may be critical areas adjacent to the border of the treatment area or surrounded by the treatment area which should not receive radiation. In order to avoid these critical areas it may be necessary to further reduce the size of the cells within the intensity map to provide even finer resolution. However, intensity maps with very small cells tend to become very complex and provide little benefit for most of the treatment area. It is thus, desirable to work with larger size cells. Since the higher resolution is typically only required at the periphery of the treatment area near regions containing critical structures, only a portion of the cells require a finer resolution. The following describes a method that allows a user to specify a resolution at the border of a treatment area and modify leaf positions at locations of cells on the border without reducing the cell size of the intensity map or creating additional cells. Since the number of cells is not increased, the time that the radiation beam is on, the total treatment time, and radiation leakage are not increased.

Figure 5A:
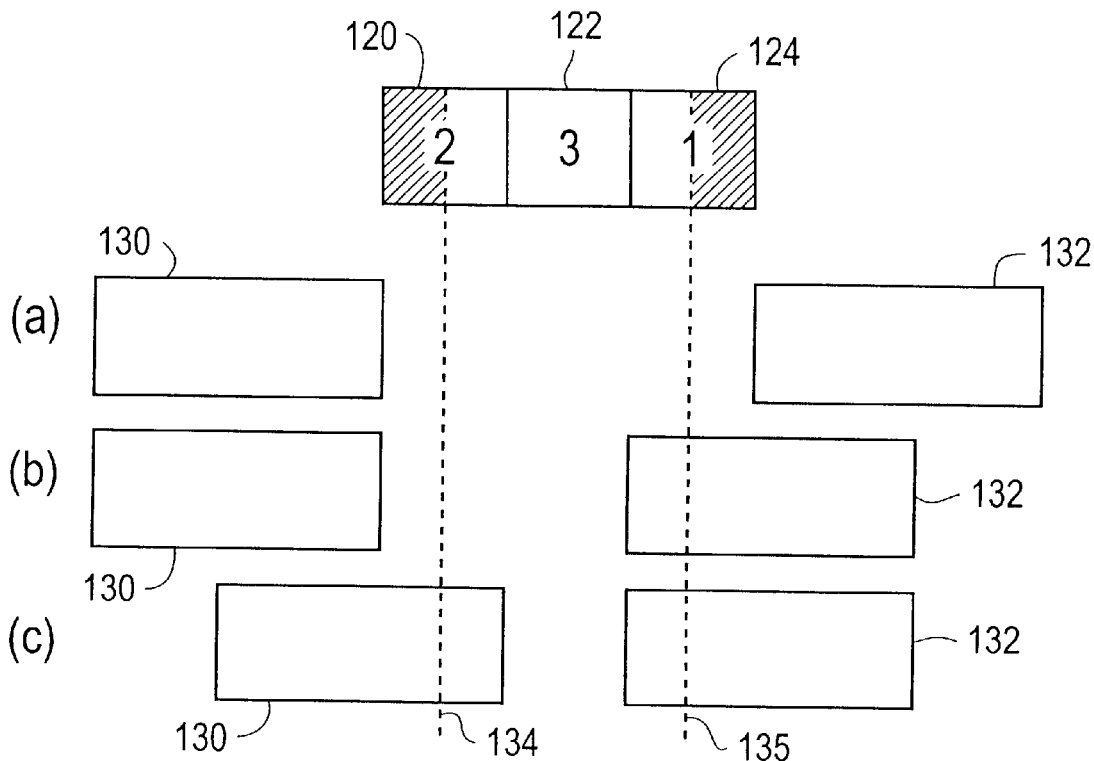
FIG. 5a is a plan view illustrating leaf positions for an intensity map prior to adjustment to block radiation from periphery edge margins of the cells.
Figure 5B:
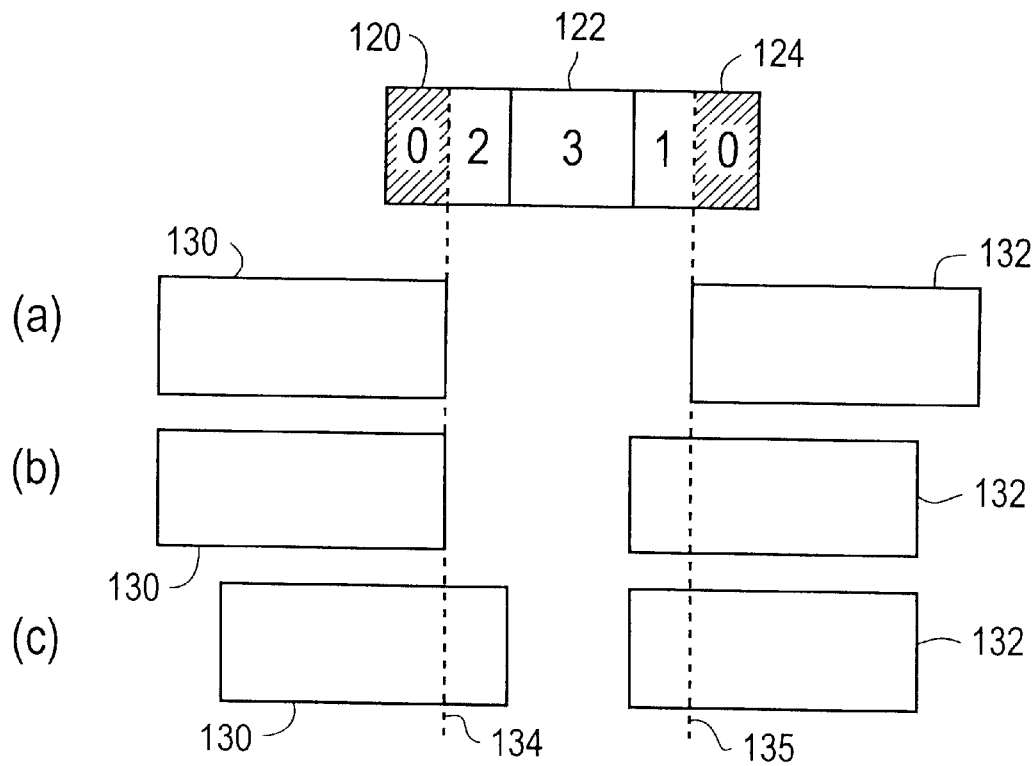
FIG. 5b is a plan view illustrating leaf positions for the intensity map of FIG. 5 after adjustment for the periphery edge margins.

FIG. 5a shows an intensity map comprising three cells 120, 122, 124. The numbers (2, 3, 1) within each cell 120, 122, 124, respectively, represent the radiation intensity level for locations within the field and are in monitor units (mu) or relative monitor unit intensities (e.g., $1 \times 10^2$ mu). The radiation treatment may be applied in three separate intensity (treatment) fields. The first is shown in the top row labeled (a). An opposing leaf pair 130, 132 is positioned such that one unit of radiation is delivered to all three cells. The leaves 130, 132 are next positioned as shown in row (b). The right leaf (as viewed in FIG. 5a) is moved to the left to cover cell 124 since that cell has already received its required dosage of radiation. The third intensity field labeled (c) allows radiation to be delivered only to the cell 122 since that cell requires three monitor units of radiation. The outer cells 120, 124 each have an edge margin defined thereon (indicated by cross-hatch and boundary lines 134, 135). The cells 120, 124 may be located, for example, on a border of a treatment area adjacent to critical areas which should not receive significant amounts of radiation. FIG. 5b illustrates adjustment of the leaves 130, 132 to accommodate the edge margins on the periphery cells 120, 124. The leaves 130, 132 are positioned such that the edge margins are covered to prevent exposure to radiation. The edge margins may receive some insubstantial amount of radiation during treatment due to leakage between the leaves, for example, but they are not exposed directly to the radiation. The leaves 130 positioned to the left (as viewed in FIG. 5b) of the edge margin boundary 134 are moved to the right until they contact the boundary 134 and the leaves 132 positioned to the right of the boundary 135 are moved to the left until they contact the boundary 135. Thus, the leaves 130 for the first two treatment fields (a) and (b) are moved to the right and leaf 132 for the first treatment field (a) is moved to the left. The edge margins of cells 120, 124 are shielded by the leaves 130, 132 during radiation delivery for each of the three intensity fields (a), (b), and (c). This process is repeated for each row of the intensity map.

Figure 6A:
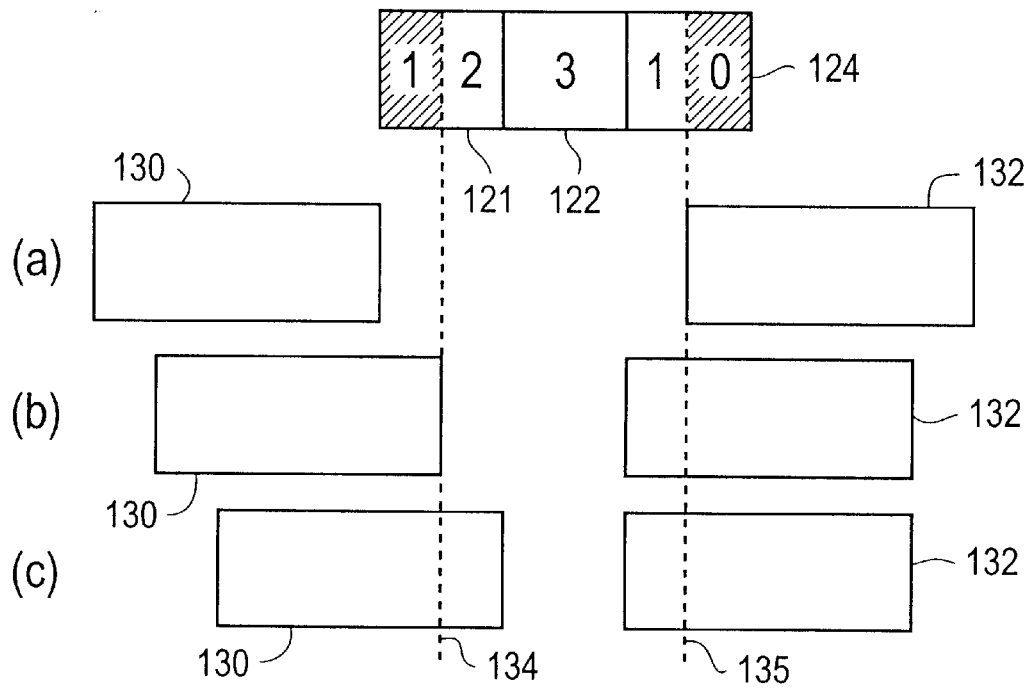
FIG. 6a is a plan view illustrating leaf positions for a cell having an edge margin with an intensity value different than an intensity value of the cell.

FIG. 6a shows an intensity map comprising three cells 121, 122, and 124. Cells 122 and 124 have the same intensity levels and edge margin as shown in FIGS. 5a and 5b. The edge margin of cell 121 has an intensity level of one rather than zero as shown in the cell 120 of FIGS. 5a and 5b. Thus, the entire cell 121 receives radiation, however, the edge margin only receives one monitor unit of radiation, whereas the remaining portion of the cell receives the full predefined cell intensity level of two monitor units. As shown in FIG. 6a, the leaf 130 for treatment field (a), is moved to the left to allow one monitor unit of radiation to be delivered to the edge margin of cell 121. The remaining leaf positions are the same as shown in FIG. 5b and described above.

Figure 6B:
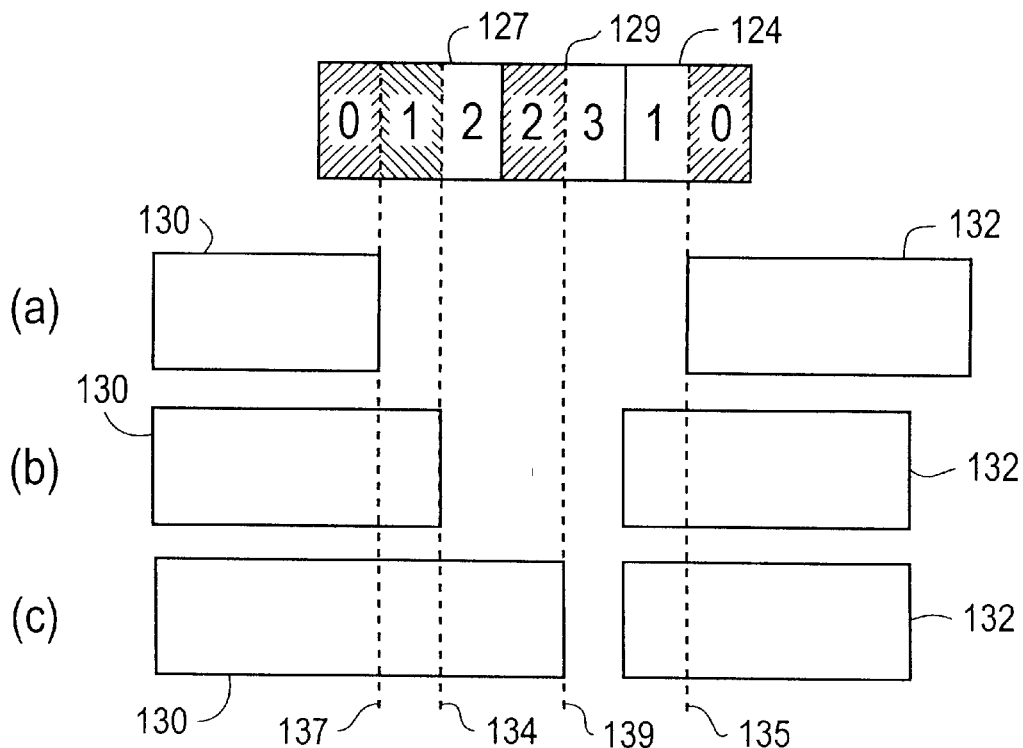
FIG. 6b is a plan view illustrating leaf positions for a cell having two edge margins.

FIG. 6b shows an intensity map comprising three cells 127, 129, and 124. Cell 124 is the same as shown in FIG. 5b. Cell 127 has two edge margins, the first being defined by boundary 137 has an intensity level of zero and the second edge margin defined by boundaries 134 and 137 has an intensity level of one. As shown in FIGS. 6a and 6b and described above, any number of edge margins may be defined on a cell, each edge margin having an intensity level different from the predefined intensity level for the cell and from the other edge margins on the cell. The longitudinal position of the leaves are adjusted to cover the edge margins of the cells in at least one of the treatment fields to reduce the amount of radiation delivered to the edge margins. In some cases, the reduced amount of radiation delivered will be zero. The first edge margin of cell 127 has an intensity level of zero and the second has an intensity level of one. Cell 129 has one edge margin having an intensity level of 2. As shown in FIG. 6b, treatment field (a) has the left leaf 130 positioned to cover only the first edge margin of cell 127 so that one monitor unit of radiation can be delivered to the central edge margin of cell 127. In treatment field (b) the left leaf 130 is moved to cover both edge margins of cell 127 and in treatment field (c) the left leaf 130 is moved to the right until it contacts the boundary 139 for the edge margin located in cell 129. Thus, the edge margin of cell 129 receives two monitor units of radiation.

Figure 7:
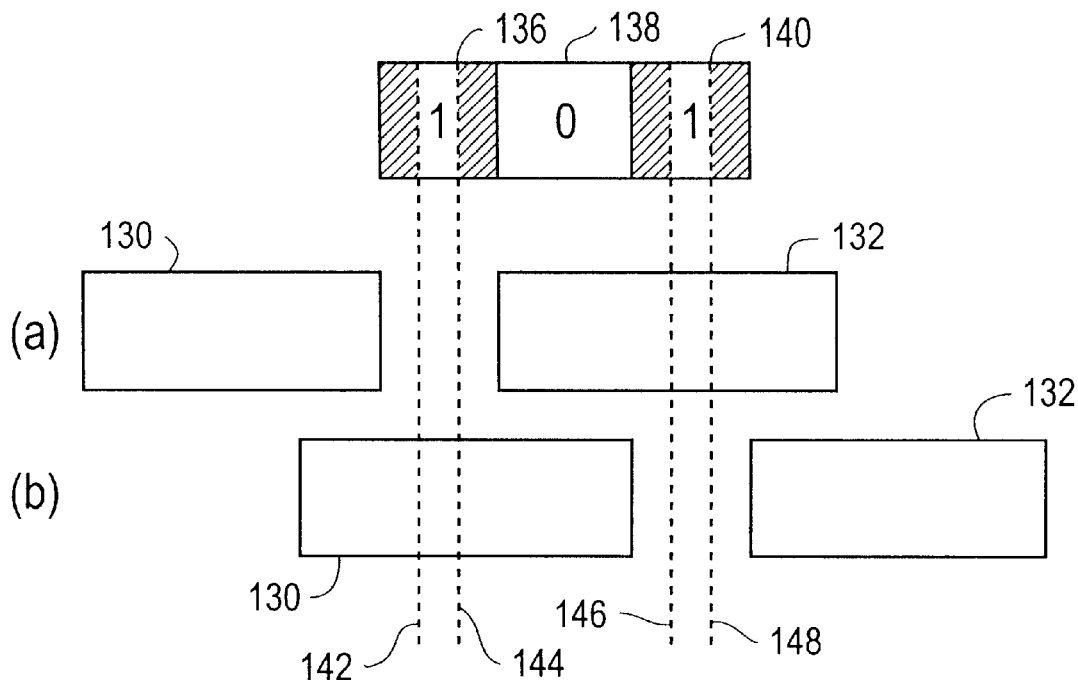
FIG. 7 is a plan view illustrating leaf positions for an intensity map prior to adjustment to block radiation from internal and periphery edge margins of the cells.
Figure 8:
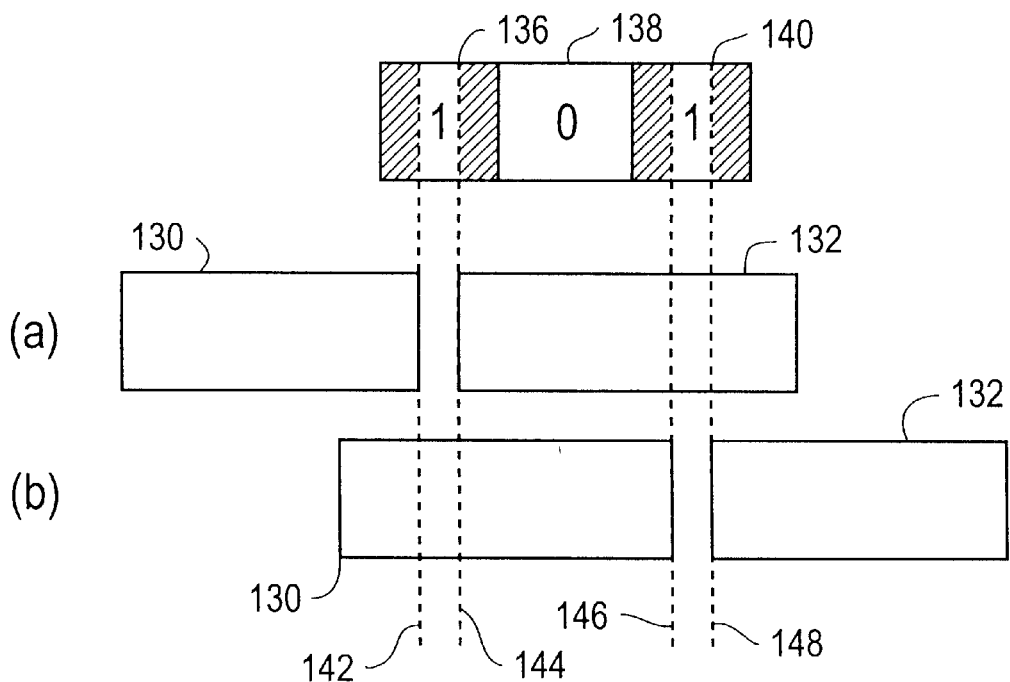
FIG. 8 is a plan view illustrating leaf positions for the intensity map of FIG. 7 after adjustment for the internal and periphery edge margins.

FIGS. 7 and 8 illustrate an intensity map having critical areas on both outer edges of the treatment area and within an internal portion of the treatment area. Cells 136 and 140 have portions adjacent to a critical area, which is not to receive radiation. Cell 138 is also used to shield the critical area from radiation. Periphery edge margin boundaries 142, 148 and internal edge margin boundaries 144, 146 are defined for cells 136, 140. As shown in FIG. 7, the leaves are first positioned to define two separate intensity fields (a) and (b). The first intensity field (a) blocks radiation from cells 138 and 140, while the second intensity field (b) blocks radiation from cells 136 and 138. Radiation is thus, delivered in one monitor unit to cell 136 with the first intensity field and in one monitor unit to cell 140 in the second intensity field. FIG. 8 illustrates adjustment of the leaves 130, 132 to shield the edge margins defined on cells 136 and 140 from radiation. In the first treatment field (a), leaves 130 and 132 are each moved towards the boundaries 142, 144, respectively, to cover the edge margins of cell 136. Thus, during the first treatment, one monitor unit of radiation is applied to only a central portion of cell 136. For the second treatment field (b), the leaves 130, 132 are moved towards the boundaries 146, 148, respectively, and one monitor unit of radiation is applied to a central portion of cell 140. In the case of internal and external edge margins, as shown in FIG. 8, leaves 130 on the left are adjusted so that a leading edge of the leaf is at least as far right as the closest edge margin boundary, and leaves 132 on the right are adjusted so that the leading edge of the leaf is at least as far left as the closest edge margin boundary.

The intensity map may also be delivered as two or more orthogonal fields by rotating the multi-leaf collimator generally about the beam axis R (FIG. 1). This allows for higher resolution intensity maps utilizing multi-leaf collimators having the same leaf width. The delivery of radiation with orthogonal intensity fields also allows edge margins to be defined perpendicular to one another. The orthogonal fields may be defined by dividing 1 cm×1 cm macrocells 100 of an intensity map into four 5 mm×5 mm microcells 102 (indicated by dashed lines in FIG. 4), for example. The 5 mm×5 mm microcells 102 are used to convert macrocell 100 into two orthogonal intensity maps, one with a resolution of 5 mm×10 mm, and the other with a resolution of 10 mm×5 mm. An example of a process for dividing the intensity map into groups of four 5 mm×5 mm microcells 102 is described in U.S. patent application Ser. No. 09/234,364, by A. Siochi, filed Jan. 20, 1999, which is incorporated herein by reference in its entirety. This grouping of 5 mm×5 mm microcells 102 allows for treatment of a field with a 5 mm×5 mm resolution using a multi-leaf collimator having one centimeter leaves, as shown in FIG. 3. For both orthogonal maps, a margin may be specified by the user and leaf positions adjusted as previously described. Edge margins are now specified in both the horizontal and vertical directions.

Figure 9:
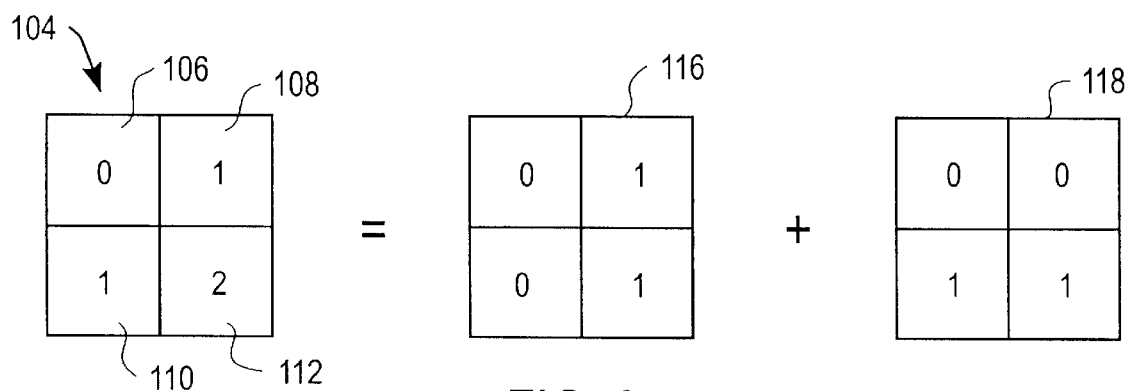
FIG. 9 is a diagram of a matrix broken down into a zero degree matrix component and a ninety degree matrix component.
Figure 10:
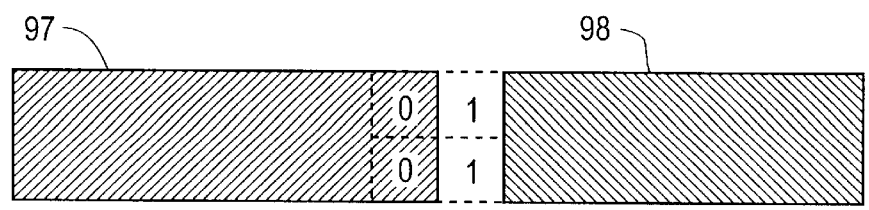
FIG. 10 is a plan view of an opposing pair of leaves configured to apply a dosage specified by the zero degree matrix of FIG. 9.
Figure 11:
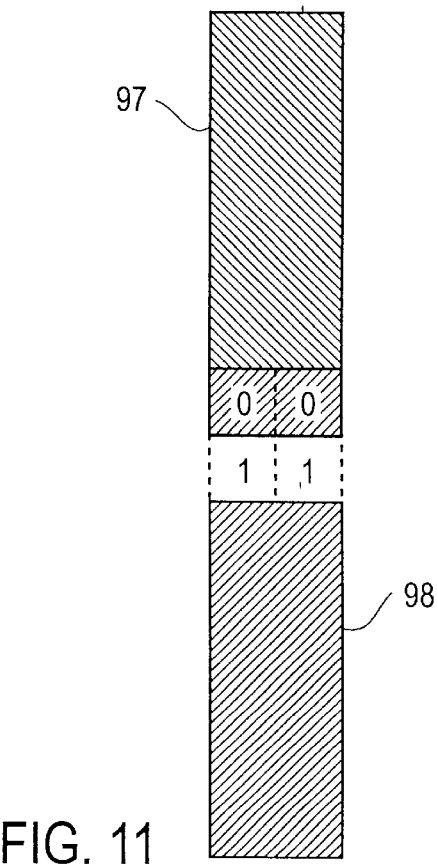
FIG. 11 is a plan view of an opposing pair of leaves configured to apply a dosage specified by the ninety degree matrix of FIG. 9.

FIG. 9 illustrates an example of a matrix, generally indicated at 104 formed from an intensity map composed of four 5 mm×5 mm microcells 106, 108, 110, 112. Each microcell 106, 108, 110, 112 identifies a section in a field to be treated with radiation. In order to provide 5 mm×5 mm resolution for the intensity map, the matrix 104 is broken down into two orthogonal matrices, 116, 118 having a 1 cm×5 mm resolution and 5 mm×1 cm resolution, respectively. A one centimeter leaf width multi-leaf collimator may then be used to deliver the intensity map with a 5 mm×5 mm resolution. For example, a pair of leaves 97, 98 positioned as shown in FIG. 10 may be used to deliver the intensity map shown in matrix 116 of FIG. 9. A dose of radiation (e.g., 1 mu) is applied to fields corresponding to microcells 108 and 112 of matrix 104. The collimator is then rotated approximately ninety degrees to deliver the intensity map shown in matrix 118 with the leaf position shown in FIG. 11. With the collimator rotated ninety degrees, a dose of radiation (e.g., 1 mu) is applied to the fields corresponding to microcells 110 and 112 of matrix 104. The two radiation applications result in a 2 mu dose to the field corresponding to microcell 112, a 1 mu dose to the fields corresponding to microcells 108 and 110, and no radiation being applied to the field corresponding to microcell 106. The decomposition of the matrix 104 into orthogonal matrices 116 and 1 18 thus provides for 5 mm×5 mm resolution treatment using collimator leaves having a one centimeter width.

In the following description, the original input intensity map is defined as a macromatrix and the groups of four microcells within the macromatrix are defined as micromatrices (or matrices). In order for the intensity map to be decomposed into orthogonal maps, the vertical gradients of each column of the micromatrix (matrix) 100 must be equal to one another and the horizontal gradients of each row of the micromatrix must also be equal to one another (FIG. 4). This provides a 1 cm×1 cm area under the intersection of one leaf pair for one collimator setting and another leaf pair for the orthogonal collimator setting. For example, if the horizontal gradients are equal for the micromatrix having cells 102 (shown in FIG. 4) the following equation must apply:

$$b-a=d-c;$$

where: a, b, c, d are the intensity values corresponding to locations in the micromatrix 100 of FIG. 4

Similarly, if the vertical gradients are equal the following equation must apply:

$$c-a=d-b.$$

A method for converting an intensity map which does not meet the above constraints (i.e., lionzontal gradients for each row are not equal or vertical gradients for each column are not equal), into an intensity map having, equal horizontal and vertical gradients is described in U.S. patent application Ser. No. 09/457,601, filed Dec. 8, 1999, which is incorporated by reference herein in its entirety. Several decompositions of an intensity map are possible to create the two orthogonal maps. An optimization method such as described in U.S. patent application Ser. No. 09/457,602, filed Dec. 8, 1999 (incorporated by reference herein in its entirety) may be used to find a decomposition which yields the shortest treatment delivery time to minimize overall treatment time and increase the life of the radiation treatment device, for example.

The intensity map may be broken down into microcells having a dimension other than 5 mm×5 mm if a different resolution is required. For example, each macrocell may be divided into nine microcells in which case the intensity map may be deliverable as two orthogonal intensity maps having a resolution of 1 cm×⅓ cm and ⅓ cm×1 cm (see, for example, U.S. patent application Ser. No. 09/234,364, referenced above). Also, a multi-leaf collimator having leaves with a width other than 1 cm may be used, and the size of the corresponding microcelds will be 1/n times the leaf width (where n is a positive integer (e.g., 2 or 3).

The treatment fields may be created by inputting data on treatment area size and shape, intensity requirements, and edge margins (based on locations of critical regions) into a processor. A beam shaper and local area therapy information system may be used to define the treatment fields and leaf positions. After the fields are defined for the cells of the intensity map, the leaf positions are adjusted to shield the edge margins and define new treatment fields that prevent radiation delivery to the edge margins of the cells.

Figure 12:
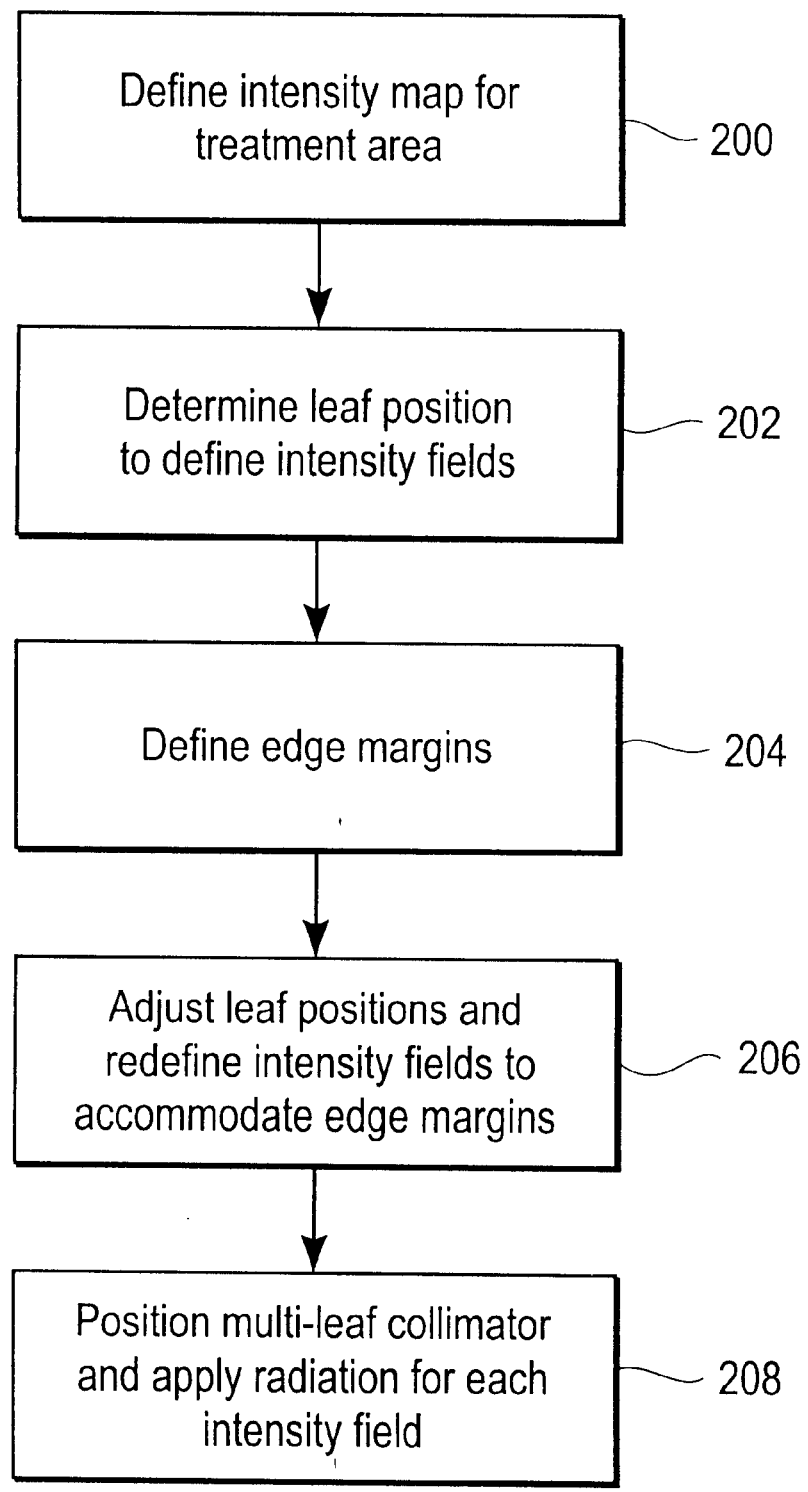
FIG. 12 is a flowchart illustrating a process for defining intensity maps and delivering radiation to a treatment area.

FIG. 12 is a flowchart illustrating a process for adjusting leaf positions for critical edge margins and delivering radiation. At step 200 an intensity map is defined on the treatment area. Leaf positions are defined to apply appropriate intensity levels for each cell (step 202). Edge margins are defined for cells having critical areas along the border of the treatment area or within the treatment area (step 204). The leaf positions are adjusted to prevent radiation exposure to the areas within the edge margins (step 206). The multi-leaf collimator is then positioned over the treatment area and the leaves are positioned and radiation is delivered for each of the defined intensity fields (step 208).

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for controlling radiation delivery from a radiation source to a treatment area with a multi-leaf collimator, comprising:
   dividing the treatment area into a plurality of cells each having a predefined treatment intensity level;
   defining one or more treatment fields by longitudinally positioning leaves of the multi-leaf collimator to block radiation from some of the cells;
   defining an edge margin on a portion of the cells, said edge margins having a intensity level different than the predefined cell intensity level; and
   adjusting a longitudinal position of the leaves such that the leaves cover said edge margin of the cells in at least one of the treatment fields to reduce the amount of radiation delivered to said edge margin.

2. The method of claim 1 wherein defining an edge margin comprises defining a periphery edge margin for cells located on a border of the treatment area.

3. The method of claim 1 wherein defining an edge margin comprises defining an area within a border of the treatment area that is shielded during radiation delivery.

4. The method of claim 1 wherein dividing the treatment area into a plurality of cells comprises grouping the cells to form a plurality of matrices, each of the matrices having at least one dimension approximately equal to a width of the collimator leaf.

5. The method of claim 4 further comprising decomposing each of the matrices into orthogonal matrices.

6. The method of claim 5 wherein defining an edge margin comprises defining separate edge margins for the cells in each of the orthogonal matrices.

7. The method of claim 1 further comprising delivering radiation with the leaves in their adjusted position.

8. The method of claim 1 wherein adjusting a longitudinal position of the leaves comprises adjusting a position of the leaves for each row of cells within the treatment area.

9. The method of claim 1 wherein adjusting a longitudinal position of the leaves comprises covering said edge margin in all of said treatment fields to substantially prevent radiation of the edge margin.

10. The method of claim 1 wherein defining an edge margin comprises defining at least two edge margins on one or more cells, each edge margin having an intensity level different from the other edge margin and remaining portion of the cell.

11. A system for controlling radiation delivery to a treatment area from a radiation source, said treatment area having a field defined thereon for radiation delivery, said field including a plurality of cells having predefined treatment intensity levels, a portion of the cells having an edge margin having an intensity level different than the predefined intensity level of the cell, the system comprising:
   a collimator having multiple leaves for blocking radiation from said source and defining an opening between the radiation source and said treatment area; and
   a processor operable to receive cell and edge margin data and position the leaves to define at least one treatment field based on the cell sizes and intensity levels and adjust the leaf positions to reduce the amount of radiation delivered to said edge margins.

12. The system of claim 11 wherein the collimator is rotatable about a radiation beam emitted from the radiation source to deliver radiation to a first treatment field with the leaves extending longitudinally along a first axis and a second treatment field with the leaves extending longitudinally along a second axis.

13. The system of claim 12 wherein the multi-leaf collimator is operable to provide radiation treatment with a resolution approximately one half of the width of the leaves.

14. The system of claim 12 wherein the first axis is generally orthogonal to the second axis.

* * * * *